United States Patent
Katoh et al.

(10) Patent No.: US 6,949,658 B2
(45) Date of Patent: Sep. 27, 2005

(54) PROCESS FOR PRODUCING OPTICALLY ACTIVE α-AMINO ACID AND OPTICALLY ACTIVE α-AMINO ACID AMIDE

(75) Inventors: Osamu Katoh, Kanagawa (JP); Toshitaka Uragaki, Kanagawa (JP); Tetsuji Nakamura, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 28 days.

(21) Appl. No.: 10/276,702

(22) PCT Filed: May 18, 2001

(86) PCT No.: PCT/JP01/04191

§ 371 (c)(1),
(2), (4) Date: Apr. 14, 2003

(87) PCT Pub. No.: WO01/87819

PCT Pub. Date: Nov. 22, 2001

(65) Prior Publication Data

US 2003/0171597 A1 Sep. 11, 2003

(30) Foreign Application Priority Data

May 22, 2000 (JP) ....................................... 2000-150285
May 18, 2000 (JP) ....................................... 2000-146663

(51) Int. Cl.$^7$ .................. C07D 233/60; C07D 209/20; C07D 207/00; C07C 229/00; C07C 227/00
(52) U.S. Cl. .................. 548/339.1; 548/496; 548/535; 562/445; 562/554; 564/164; 564/193
(58) Field of Search .............................. 548/339.1, 496, 548/535; 562/445, 554; 564/164, 193

(56) References Cited

FOREIGN PATENT DOCUMENTS

| | | |
|---|---|---|
| EP | 193113 | 9/1986 |
| GB | 2182036 | 5/1987 |
| JP | 59-159789 | 9/1984 |
| JP | 61-197530 | 9/1986 |
| JP | 61-274690 | 12/1986 |
| JP | 61-293394 | 12/1986 |
| JP | 63-87998 | 4/1988 |
| JP | 1-186850 | 7/1989 |
| JP | 01-186850 | * 7/1989 |
| JP | 2001-11034 | 1/2001 |

* cited by examiner

Primary Examiner—Richard L. Raymond
Assistant Examiner—Zachary C. Tucker
(74) Attorney, Agent, or Firm—Oblon, Spivak, McClelland, Maier & Neustadt, P.C.

(57) ABSTRACT

The present invention provides a process for efficiently producing an optically active α-amino acid and an optically active α-amino acid amide. After contacting with cells or processed cells thereof having an ability to asymmetrically hydrolyse, a water solvent is substituted with at least one solvent selected from the group consisting of linear, branched, or cyclic alcohol having 3 or more carbon atoms and the optically active α-amino acid is preferentially precipitated from the alcohol solution.

The addition of basic compounds, particularly potassium compounds to the alcohol solution containing the optically active α-amino acid amide, which is obtained after the separation of the optically active α-amino acid, enables the purification of the amide without the inclusion of amino acid into amino acid amide. Thus, the amide is subjected to the step of racemization and then recycled.

34 Claims, No Drawings

PROCESS FOR PRODUCING OPTICALLY ACTIVE α-AMINO ACID AND OPTICALLY ACTIVE α-AMINO ACID AMIDE

TECHNICAL FIELD

The present invention relates to a process for producing optically active α-amino acid and optically active α-amino acid amide. Optically active α-amino acid, optically active α-amino acid amide, and a racemic amino acid amide are used as starting material for pharmaceuticals, pesticides, and the like.

BACKGROUND ART

There have been many reports on the production of optically active α-amino acid through chemical synthesis and biological synthesis.

For example, a process for optically resolving racemic α-amino acid amide using microorganisms and the like which has an ability to asymmetrically hydrolyse α-amino acid amide is a known process of biological synthesis. This process is useful as a general process for producing optically active α-amino acid because: α-amino acid with high optical purity can be easily produced by obtaining microorganisms with high stereoselectivity; starting racemic α-amino acid amide can be easily produced; this process can be applied for the production of both natural-type and non-natural-type optically active α-amino acids; and the like.

In the process for optically resolving racemic α-amino acid or optically impure α-amino acid amide using microorganisms and the like which has an ability to asymmetrically hydrolyse α-amino acid amide, however, both the optically active α-amino acid and the optically active α-amino acid amide of interest are present in the solution after the completion of the reaction. Thus, the optically active α-amino acid needs to be separated from the optically active α-amino acid amide.

One separation process can be carried out as follows: after the enzymatic asymmetric hydrolysis is carried out in an aqueous medium, the reaction solution is concentrated, a poor solvent for amino acid (i.e., an organic solvent such as alcohol) is added, the crystallized amino acid is taken, and unreacted amino acid amide is obtained as a filtrate in a dissolved state in a water-alcohol mixed solvent. Further, a process for producing optically active amino acid and amino acid amide in combination with racemization has been reported as a more efficient production process.

Examples of reported processs are: a process in which α-amino acid amide is removed by solvent extraction, followed by the collection of α-amino acid at the isoelectric point (see JP Patent Application Laying Open (Kokai) Nos. 58-209989 and 57-13000); a process in which ethanol is added and amino acid is preferentially crystallized (see JP Patent Application Laying Open (Kokai) Nos. 63-87998, 61-274690, 60-184392, and 59-159789); a process in which adsorption separation is carried out using an ion-exchange resin (see JP Patent Application Laying Open (Kokai) No. 1-226482); and a process in which α-amino acid amide is adsorbed on a cation-exchange resin, the cation-exchange resin is brought into contact with an enzyme to perform stereospecific hydrolysis, and a reaction is simultaneously conducted with the separation process, thereby producing the optically active amino acid (see JP Patent Application Laying Open (Kokai) No. 8-23996).

A process has been also reported in which, after the optical resolution, water which is contained in an aqueous solution of the obtained optically active α-amino acid, is removed under reduced pressure, the residue is washed with a heated organic solvent to selectively remove α-amino acid amide, and the remaining optically active α-amino acid is then recovered (see JP Patent Application Laying Open (Kokai) No. 61-293394).

This report also describes that a strongly basic compound is added to the organic solvent of the washed and recovered optically active α-amino acid amide, racemization of α-amino acid amide is carried out by heating, and the resulting mixture of D- and L-α-amino acid amide is recycled in asymmetric hydrolysis.

A process for racemizing α-amino acid amide by heating in the presence of alkali in an organic solvent is also described in JP Patent Application Laying Open (Kokai) No. 62-252751).

Further, JP Patent Application Laying Open (Kokai) No. 61-197530 describes that racemization efficiently proceeds under alkali conditions in an organic solvent.

In all these reports, the water content in the solution of the optically active α-amino acid amide should be kept low in order to inhibit the hydrolysis of α-amino acid amide, which is a side reaction during racemization. For example, the water content in an organic solvent has been specified at 10% or lower in JP Patent Application Laying Open (Kokai) No. 62-252751.

However, the process for separating the optically active α-amino acid from α-amino acid amide has various drawbacks, and it is not an industrially efficient production process.

In the process for collecting α-amino acid at the isoelectric point after separating α-amino acid from α-amino acid amide by solvent extraction, a large quantity of solvent is required for extraction. Accordingly, it is disadvantageous in terms of apparatus and cost. In the process for performing adsorption separation using an ion-exchange resin, many steps, such as adsorption, elimination, and recovery, are required. This process is unfavorable from the industrial point of view since it may bring about increased equipment investment, lowered recovery efficiency, contamination with impurities, and the like.

In contrast, in the process for preferentially crystallizing α-amino acid with the addition of ethanol to the concentrated reaction solution, operation is simpler and equipment investment is smaller than other processss since, for example, the process of concentration-crystallization can be carried out in the same tank. In this process, however, required ethanol volume should be several times that of the concentrate. This is one factor for the increased cost. Regarding this technique, there is a report concerning the limited use of this process for natural-type amino acids only, and the description on the purity of the obtained amino acid is available for valine only. Whether or not high purity amino acid can be efficiently obtained is not clear at all for other amino acids. Therefore, this process cannot be said to be versatile.

When the separated optically active α-amino acid amide is to be racemized and re-used in optical resolution in the above-mentioned process, it is obvious that ethanol has a low boiling point and is not suitable as a solvent for racemization. For example, JP Patent Application Laying Open (Kokai) No. 62-252751 describes an example of racemization using an ethanol solution, wherein the reaction is carried out by heating a vessel between 110 to 120° C. after sealing the reaction vessel in order to increase the reaction temperature. This process requires a particular apparatus for an industrial scale. Accordingly, without any equipment investment, it would be difficult to perform the ethanol-based reaction at normal pressure.

Further, since the water content of the separated and collected ethanol solution containing optically active α-amino acid amide is high, and the like, racemization of the optically active α-amino acid amide requires the dehydration of solution, substitution of solvents, and the like or the isolation and drying of the optically active α-amino acid amide crystals. These, therefore, complicate the processes.

In addition, the above process cannot always completely crystallize amino acid only, and amino acid could be contaminated with amino acid amide.

When only one optically active substance is needed, for example, it is very favorable if the optically active amino acid amide can be racemized and re-used as a starting material for asymmetric hydrolysis. However, the optical purity could be lowered by the contamination by amino acid.

In one process, which is carried out by removing water and washing the residue with a heated organic solvent, followed by selective washing and removal of α-amino acid amide, racemization can be carried out without isolating the optically active α-amino acid amide from the solution. However, it becomes technically difficult to completely dehydrate the solution and concentrate to dryness in the industrial scale production. This production process is impractical considering operability, equipment investment, and the like.

Accordingly, the processs for producing optically active α-amino acid and purifying racemized α-amino acid amide by the known technique are either inefficient or impractical for the collection of optically active α-amino acid and α-amino acid amide after the reaction, and are not industrially advantageous processs.

The present invention provides an effective and efficient process for producing optically active α-amino acid and optically active α-amino acid amide, which overcomes the above-mentioned disadvantages.

DISCLOSURE OF THE INVENTION

The present inventors have conducted concentrated studies in order to solve the above problems. As a result, they found that optically active α-amino acid can be produced in very high yield by substituting the water solvent of an aqueous solution containing optically active α-amino acid and optically active α-amino acid amide with an alcohol solvent having 3 or more carbon atoms and preferentially obtaining the optically active α-amino acid from an alcohol solution.

They further found that, racemization of the optically active α-amino acid amide can be performed in order to more efficiently produce the optically active α-amino acid without isolating the optically active α-amino acid amide from an alcoholic solution containing the optically active α-amino acid amide obtained as a separated mother liquor after asymmetric hydrolysis and crystallization and separation of the optically active α-amino acid. They have also conducted concentrated studies on a process for purifying amino acid amide from a solution containing amino acid and amino acid amide. As a result, they found that: the addition of a basic compound into a solution containing amino acid and amino acid amide resulted in improved amino acid solubility in an organic solvent; the precipitation of amino acid amide from the solution resulted in high purity amino acid amide with little contamination of amino acid; and the addition of the basic compound was very effective for separating amino acid and amino acid amide and racemizing amino acid amide. They further found that the optically active α-amino acid amide could be more efficiently racemized since water generated upon reaction with the basic compound can be removed by dehydration such as azeotropic dehydration after the addition of a basic compound and that, after racemization, the collected mixture of D and L-α-amino acid amide could be recycled as a starting material for asymmetric hydrolysis of α-amino acid amide.

More specifically, the present invention relates to the following (1) to (25).

(1) A process for producing optically active α-amino acid and optically active α-amino acid amide which comprises substituting the water solvent of an aqueous solution containing the optically active α-amino acid and the optically active α-amino acid amide with at least one alcohol selected from the group consisting of linear, branched, or cyclic alcohol having 3 or more carbon atoms, and precipitating the optically active α-amino acid from the alcohol solution, wherein α-amino acid is represented by formula (I):

wherein R1 and R2 may be the same or different and represent a hydrogen atom, lower alkyl, substituted lower alkyl, lower alkenyl, substituted lower alkenyl, cycloalkyl, phenyl, substituted phenyl, heterocycle, and substituted heterocycle; and α-amino acid amide is represented by formula (II):

wherein R1 and R2 may be the same or different and represent a hydrogen atom, lower alkyl, substituted lower alkyl, lower alkenyl, substituted lower alkenyl, cycloalkyl, phenyl, substituted phenyl, heterocycle, and substituted heterocycle.

(2) The process for producing optically active α-amino acid and optically active α-amino acid amide according to (1), wherein the α-amino acid and α-amino acid amide are: amino acid having an aromatic ring represented by formula (III)

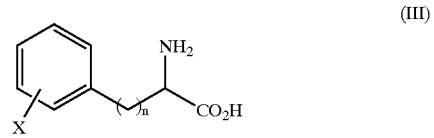

wherein n is 0 to 1 and X represents hydrogen, halogen, alkyl, hydroxyl, and alkoxy and amino acid amide having an aromatic ring represented by formula (IV)

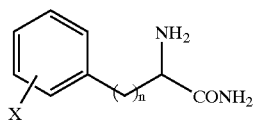

(IV)

wherein n is 0 to 1 and X represents hydrogen, halogen, alkyl, hydroxyl, and alkoxy; or aliphatic amino acid represented by formula (V):

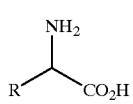

(V)

wherein R represents linear or branched alkyl having 2 to 5 carbon atoms and aliphatic amino acid amide represented by formula (VI)

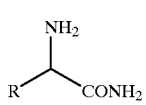

(VI)

wherein R represents linear or branched alkyl having 2 to 5 carbon atoms.

(3) The process for producing optically active α-amino acid and optically active α-amino acid amide according to (2), wherein the α-amino acid and the α-amino acid amide are selected from the group consisting of: α-tert-leucine and α-tert-leucine amide; α-phenylalanine and α-phenylalanine amide; α-phenylglycine and α-phenylglycine amide; α-p-fluoro-phenylglycine and α-p-fluoro-phenylglycine amide; α-o-chloro-phenylglycine and α-o-chloro-phenylglycine amide; α-p-hydroxy-phenylalanine and α-p-hydroxy-phenylalanine amide; α-2-amino-n-lactic acid and α-2-amino-n-lactic acid amide; and α-isoleucine and α-isoleucine amide.

(4) The process for producing optically active α-amino acid and optically active α-amino acid amide according to (1), wherein the alcohol is selected from the group consisting of n-butanol, isopropanol, isobutyl alcohol, 1-pentanol, and cyclohexanol.

(5) The process for producing optically active α-amino acid and optically active α-amino acid amide according to (2), wherein the alcohol is selected from the group consisting of n-butanol or isopropanol, isobutyl alcohol, 1-pentanol, and cyclohexanol.

(6) The process for producing optically active α-amino acid and optically active α-amino acid amide according to (3), wherein the alcohol is selected from the group consisting of n-butanol or isopropanol, isobutyl alcohol, 1-pentanol, and cyclohexanol.

(7) The process for producing optically active α-amino acid and optically active α-amino acid amide according to any one of (1) to (6), wherein an aqueous solution containing the optically active α-amino acid and the optically active α-amino acid amide is obtained by contacting optically impure α-amino acid amide with cells or processed cells thereof having an ability to asymmetrically hydrolyse.

(8) The process for producing optically active α-amino acid and optically active α-amino acid amide according to any one of (1) to (6), wherein the water content of the separated mother liquor after the precipitation of the optically active α-amino acid is 10% by mass or lower.

(9) The process for producing optically active α-amino acid and optically active α-amino acid amide according to (7), wherein the water content of the separated mother liquor after the precipitation of the optically active α-amino acid is 10% by mass or lower.

(10) A process for purifying α-amino acid amide, which comprises adding potassium hydroxide or tert-butoxypotassium to the separated mother liquor, in which optically active α-amino acids had been precipitated, obtained by the process according to any one of (1) to (6), recemizing, and then precipitating α-amino acid amide preferentially from the solution.

(11) A process for purifying α-amino acid amide, which comprises adding potassium hydroxide or tert-butoxypotassium to the separated mother liquor, in which optically active α-amino acids had been precipitated, obtained by the process according to (7), recemizing, and then precipitating α-amino acid amide preferentially from the solution.

(12) A process for purifying α-amino acid amide, which comprises adding potassium hydroxide or tert-butoxypotassium to the separated mother liquor, in which optically active α-amino acids had been precipitated, obtained by the process according to (8), recemizing, and then precipitating α-amino acid amide preferentially from the solution.

(13) A process for purifying α-amino acid amide, which comprises adding potassium hydroxide or tert-butoxypotassium to the separated mother liquor, in which optically active α-amino acids had been precipitated, obtained by the process according to (9), recemizing, and then precipitating α-amino acid amide preferentially from the solution.

(14) The process for purifying amino acid amide according to (10), wherein the amino acid content in the precipitated crystalline amino acid amide is 1.5% or lower.

(15) The process for purifying amino acid amide according to (11), wherein the amino acid content in the precipitated crystalline amino acid amide is 1.5% or lower.

(16) The process for purifying amino acid amide according to (12), wherein the amino acid content in the precipitated crystalline amino acid amide is 1.5% or lower.

(17) The process for purifying amino acid amide according to (13), wherein the amino acid content in the precipitated crystalline amino acid amide is 1.5% or lower.

(18) A process for producing optically active α-amino acid and optically active α-amino acid amide, wherein the α-amino acid amide, which was obtained by the process according to (10), is recycled as a starting material for asymmetric hydrolysis.

(19) A process for producing optically active α-amino acid and optically active α-amino acid amide, wherein the α-amino acid amide, which was obtained by the process according to (11), is recycled as a starting material for asymmetric hydrolysis.

(20) A process for producing optically active α-amino acid and optically active α-amino acid amide, wherein the α-amino acid amide, which was obtained by the process according to (12), is recycled as a starting material for asymmetric hydrolysis.

(21) A process for producing optically active α-amino acid and optically active α-amino acid amide, wherein the α-amino acid amide, which was obtained by the process according to (13), is recycled as a starting material for asymmetric hydrolysis.

(22) A process for producing optically active α-amino acid and optically active α-amino acid amide, wherein the α-amino acid amide, which was obtained by the process according to (14), is recycled as a starting material for asymmetric hydrolysis.

(23) A process for producing optically active α-amino acid and optically active α-amino acid amide, wherein the α-amino acid amide, which was obtained by the process according to (15), is recycled as a starting material for asymmetric hydrolysis.

(24) A process for producing optically active α-amino acid and optically active α-amino acid amide, wherein the α-amino acid amide, which was obtained by the process according to (16), is recycled as a starting material for asymmetric hydrolysis.

(25) A process for producing optically active α-amino acid and optically active α-amino acid amide, wherein the α-amino acid amide, which was obtained by the process according to (17), is recycled as a starting material for asymmetric hydrolysis.

General embodiments of the present invention are described below.

Types of α-amino acid used in the present invention are not limited, but those represented by the following formula (I) are preferred:

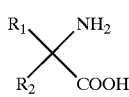
(I)

wherein R1 and R2 may be the same or different and represent a hydrogen atom, lower alkyl, substituted lower alkyl, lower alkenyl, substituted lower alkenyl, cycloalkyl, phenyl, substituted phenyl, heterocycle, and substituted heterocycle.

Examples of substances represented by formula (I) include alanine, valine, leucine, isoleucine, methionine, tryptophan, phenylalanine, serine, cysteine, tyrosine, lysine, histidine, 2-amino-n-lactic acid, cyclohexylalanine, norvaline, norleucine, 6-hydroxynorleucine, neopentylglycine, penicillamine, tert-leucine, phenylglycine, o-chlorophenylglycine, m-chlorophenylglycine, p-chlorophenylglycine, p-fluorophenylglycine, p-chlorophenylalanine, p-hydroxyphenylalanine, and o,p-dichlorophenylglycine.

In the present invention, the types of α-amino acid amide are not limited, but those represented by the following formula (II) are preferred:

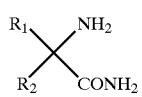
(II)

wherein R1 and R2 may be the same or different and represent a hydrogen atom, lower alkyl, substituted lower alkyl, lower alkenyl, substituted lower alkenyl, cycloalkyl, phenyl, substituted phenyl, heterocycle, and substituted heterocycle.

Examples of substances represented by formula (II) include alanine amide, valine amide, leucine amide, isoleucine amide, methionine amide, tryptophan amide, phenylalanine amide, serine amide, cysteine amide, tyrosine amide, lysine amide, histidine amide, 2-amino-n-lactic acid amide, cyclohexylalanine amide, norvaline amide, norleucine amide, 6-hydroxynorleucine amide, neopentylglycine amide, penicillamine amide, tert-leucine amide, phenylglycine amide, o-chlorophenylglycine amide, m-chlorophenylglycine amide, p-chlorophenylglycine amide, p-fluorophenylglycine amide, p-chlorophenylalanine amide, p-hydroxyphenylalanine amide, and o,p-dichlorophenylglycine amide.

Preferred among these are:

amino acid having an aromatic ring represented by formula (III)

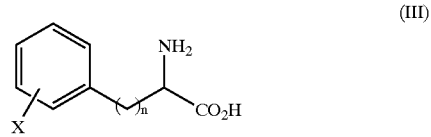
(III)

wherein n is 0 or 1 and X represents hydrogen, halogen, alkyl, hydroxyl, and alkoxy and amino acid amide having an aromatic ring represented by formula (IV)

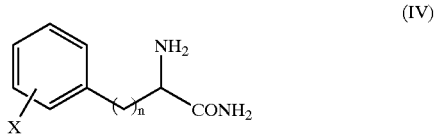
(IV)

wherein n is 0 or 1 and X represents hydrogen, halogen, alky, hydroxyl, and alkoxy; or aliphatic amino acid represented by formula (V)

(V)

wherein R represents linear or branched alkyl having 2 to 5 carbon atoms and aliphatic amino acid amide represented by formula (VI)

(VI)

wherein R represents linear or branched alkyl having 2 to 5 carbon atoms.

α-amino acid amide can be optically resolved by functions of microorganisms which stereospecifically act on racemic or optically impure α-amino acid amide in an aqueous medium and provide α-amino acid amide having optical properties corresponding to the optically active α-amino acid. The types of microorganism are not particularly limited as long as they catalyze the above reaction, and examples thereof include *Enterobacter cloacae* N-7901 (FERM BP-873) and *E. coli* JM 109/pLA205 (FERM BP-7132). These microorganisms are used just as they are or as processed cells (e.g., washed cells, dried cells, homogenized cells, cell extract, crude or purified enzyme, and immobilized products thereof).

The optical resolution is carried out by contacting α-amino acid amide with the above-mentioned cells or processed cells thereof in an aqueous medium. The concentration of α-amino acid amide is generally 0.1 to 60% by mass and preferably 1 to 40% by mass. The concentration of cells or processed cells thereof is generally 1/10,000 to 1 based on the mass of amino acid amide and preferably 1/1,000 to 1/10 mass, although the concentration varies depending on the active mass. pH value of the reaction solution is generally 4 to 11, preferably 6 to 10, and the reaction temperature is generally 10 to 60° C., and preferably 20 to 50° C.

After the completion of the reaction, a process for removing the cells or the processed cells thereof from the reaction solution is not particularly limited. For example, it can be carried out by centrifugation, filtration, and the like. The reaction solution from which the cells or the processed cells thereof have already been removed, may be subjected to vacuum concentration, if necessary.

Water in the resultant reaction solution or concentrate is substituted with at least one solvent selected from linear, branched, or cyclic alcohol having 3 or more carbon atoms, preferably 3 to 6 carbon atoms, more preferably 4 to 6 carbon atoms. Solvents include propanol, butanol, pentanol, and hexanol. n-butanol and isopropyl alcohol are preferred.

Solvents are substituted by operations such as azeotropy, and the operation is continued until water contained in the aqueous solution containing optically active α-amino acid and optically active α-amino acid amide, which is obtained after asymmetric hydrolysis of α-amino acid amide, is substituted with an alcohol solvent. Preferably, 90% by mass or more of water is substituted.

Processs for obtaining the optically active α-amino acid after substitution with an alcohol solvent are not particularly limited, but examples thereof include a process by precipitation.

The concentration and the temperature of the optically active α-amino acid when precipitating the optically active α-amino acid are not particularly limited as long as the optically active α-amino acid can be collected with high yield. The concentration is 1 to 50% by mass and preferably 5 to 30% by mass, and the temperature is −20 to 60° C., and preferably 0 to 40° C. with respect to operation efficiency and the like. The solution is heated and stirred at a temperature higher than that at the time of precipitation, and the optically active α-amino acid is precipitated at the above-mentioned temperature, thereby obtaining high purity optically active α-amino acid. Further, the precipitated optically active α-amino acid can be collected either by a continuous or batch operation.

The optically active α-amino acid precipitated as crystals as a result of the above operation is collected by centrifugation, filtration, or the like. Accordingly, the optically active α-amino acid can be separated from the optically active α-amino acid amide also dissolved in the solution.

The optically active α-amino acid amide in the separated mother liquor is optionally substituted with a solvent which has lower solubility against the optically active α-amino acid amide. Alternatively, optically active α-amino acid amide can be collected in a solid state by removing the solvent.

Racemization of optically active α-amino acid amide is carried out by adding a basic compound to an alcohol solution containing optically active α-amino acid amide, which is prepared as a separated mother liquor.

The basic compounds are not particularly limited as long as amino acid becomes salt which is easily dissolved in the organic solvent, and can be selected from at least one of alkali metal, alkali metal hydroxide, alkali metal hydride, alkali metal salt, and alcoholate of alkali metal. Examples of alkali metal include metallic sodium and metallic potassium, examples of alkali metal hydride include sodium hydride and potassium hydride, examples of alkali metal salt include sodium carbonate and potassium carbonate, examples of alkali metal hydroxide include sodium hydroxide and potassium hydroxide, and examples of alcoholate of alkali metal include sodium methylate, sodium ethylate, potassium methylate, potassium-tert-butyrate. Among these, potassium compounds are particularly preferred.

The amount of the basic compound to be added is 0.01 to 1.0 molar equivalent, preferably 0.05 to 0.5 molar equivalent based on the amount of amino acid amide. When α-amino acid is also present in the alcohol solution containing α-amino acid amide, 1.0 molar equivalent or more basic compound based on α-amino acid can be further added to the above-mentioned amount. Dehydration such as azeotropic dehydration after the addition of the basic compound can remove moisture from the basic compound. Accordingly, optically active α-amino acid amide can be more efficiently racemized. Thus, racemization of the optically active α-amino acid amide, which was collected as an alcohol solution, can be carried out in a simple procedure while being dissolved in an alcohol solvent without complex processes.

Conditions for racemization of optically active α-amino acid amide are not particularly limited although the conditions vary depending on various factors such as types of α-amino acid amide and basic compounds, concentration, and the like. Racemization is generally carried out at a reaction temperature of 80 to 200° C., preferably 100 to 150° C. for 10 minutes to 24 hours.

Amino acid amide is obtained by adding a suitable organic solvent to a solution containing amino acid and amino acid amide to which a basic compound has been included, and preferentially precipitating amino acid amide. When precipitating, any organic solvent can be used as long as the amino acid salt, which is a salt of the basic compound, is soluble therein while amino acid amide is less soluble therein.

Amino acid amide can be precipitated from the solution by concentration, cooling, or the like.

After the reaction, the mixture of D- and L-α-amino acid amide is collected in accordance with conventional techniques and recycled in asymmetric hydrolysis of amino acid amide.

BEST MODE FOR CARRYING OUT THE INVENTION

The present invention is described in more detail with reference to the following Examples.

REFERENCE EXAMPLE 1

Preparation of an Aqueous Solution Containing Optically Active α-amino Acid and Optically Active α-amino Acid Amide In accordance with the process described in JP Patent Application Laying Open (Kokai) No. 62-55097, *Enterobacter cloacae* N-7901 (FERM BP-873) was cultured. 1 L of culture solution was centrifuged, and the wet cells were then suspended in distilled water to prepare a 800 g cell suspension. 200 g of D,L-tert-leucine amide was dissolved in this suspension, and the solution was then allowed to react at 40° C. for 52 hours. After the reaction, cells were removed by centrifugation and 970 g of an aqueous solution containing 10% by mass each of L-tert-leucine and D-tert-leucine amide was obtained.

The concentrations of tert-leucine and tert-leucine amide were analyzed in accordance with analytical condition 1 of high performance liquid chromatography (HPLC) and the optical purity was independently analyzed according to analytical condition 2 of HPLC. Water content of the solution was measured using a Karl Fischer moisture meter (Mitsubishi Moisture Meter CA-60, Mitsubishi Kasei).
Analytical condition 1 of HPLC:
  Column: Inertsil ODS-3V (4.6φ×250 mm)
  Mobile phase: 0.1% aqueous solution of phosphoric acid
  Flow rate: 1 mL/min
  Detection: RI
Analytical condition 2 of HPLC:
  Column: SUMICHIRAL OA-5000 (4.6φ×250 mm)
  Mobile phase: water-methanol (85:15)
  Flow rate: 1 mL/min
  Detection: UV 254 nm

EXAMPLE 1

An aqueous solution containing L-tert-leucine and D-tert-leucine amide, 200 g, obtained in Reference Example 1 was vacuum concentrated to 72 g. Thereafter, 300 g of isopropyl alcohol was added to the solution. The solution was further vacuum concentrated to obtain a final concentrate of 140 g. The water content of the concentrate was 6.5% by mass. After this concentrate was stirred at 50° C. for 1 hour, the solution was cooled and stirred at 15° C. for an additional 4 hours. Precipitated crystals were collected by suction filtration and 18.4 g (dry mass) of L-tert-leucine was obtained (yield 92%). The amount of D-tert-leucine amide contained in crystalline L-tert-leucine was 0.01% by mass or lower.

EXAMPLE 2

An aqueous solution containing L-tert-leucine and D-tert-leucine amide, 400 g, obtained in Reference Example 1 was vacuum concentrated to 140 g. Thereafter, 300 g of n-butanol was added to the solution. The solution was further vacuum concentrated to obtain a final concentrate of 265 g. The water content of the concentrate was 0.9% by mass. n-butanol, 10 g, was added to the concentrate, and the resultant solution was stirred at 60° C. for 1 hour. Thereafter, the solution was cooled and stirred at 20° C. for an additional 3 hours. Precipitated crystals were collected by centrifugal filtration and 39.2 g (dry mass) of L-tert-leucine was obtained (yield 98%). The amount of D-tert-leucine amide contained in crystalline L-tert-leucine was 0.05% by mass.

EXAMPLE 3

An aqueous solution containing L-tert-leucine and D-tert-leucine amide, 500 g, obtained in Reference Example 1 was vacuum concentrated to 250 g. Thereafter, 250 g of n-butanol was added to the solution. The solution was further vacuum concentrated, and when the amount of the distillate became 240 g, 250 g of n-butanol was added to the solution again. After the addition, vacuum concentration was carried out again to obtain a final concentrate of 350 g. The water content of the concentrate was 0.6% by mass. After being stirred at 60° C. for 2 hours, the concentrate solution was cooled and stirred at 20° C. for an additional 2 hours. Precipitated crystals were collected by centrifugal filtration and 48.9 g (dry mass) of L-tert-leucine was obtained (yield 98%). The amount of D-tert-leucine amide contained in crystalline L-tert-leucine was less than 0.01% by mass.

D-tert-leucine amide, 49.0 g, was contained in 295 g of collected separated mother liquor.

EXAMPLE 4

Sodium hydroxide, 3.0 g, was added to 295 g of an n-butanol solution of D-tert-leucine amide (separated mother liquor) obtained in Example 3, and the mixture was heated under reflux for 4 hours. The reaction solution was vacuum concentrated to 80 g, and 100 g of n-heptane was added to the concentrate, and the mixture was then stirred at 5° C. for 10 hours. Precipitated crystals were collected by suction filtration and 38.7 g (dry mass) of a mixture of D- and L-tert-leucine amide was obtained (yield from the separated mother liquor: 79%). The abundance ratio of crystalline D-tert-leucine amide to crystalline L-tert-leucine amide was 50.2:49.8.

EXAMPLE 5

Crystal of the mixture of D- and L-tert-leucine amide, 20 g, obtained in Example 4 was mixed with a 80 g cell suspension prepared in Reference Example 1, and cell reaction was carried out in the same manner as in Reference Example 1. Fifty two hours later, the reaction solution contained 10% by mass each of L-tert-leucine and D-tert-leucine amide.

EXAMPLE 6

Potassium hydroxide, 3.0 g, was added to 295 g of an n-butanol solution containing D-tert-leucine amide (separated mother liquor) obtained in Example 3, and the solution was then vacuum concentrated to 206 g. The water content of the concentrate was 0.06% by mass. After the concentrate was heated under reflux for 6 hours, the reaction solution was vacuum concentrated to 81 g, 100 g of n-heptane was further added to the concentrate, and the mixture was stirred at 5° C. for 3 hours. Precipitated crystals were collected by suction filtration and 40.2 g (dry mass) of the mixture of D- and L-tert-leucine amide was obtained (yield from the separated mother liquor: 82%). The abundance ratio of crystalline D-tert-leucine amide to crystalline L-tert-leucine amide was 50.0:50.0.

EXAMPLE 7

In the same manner as in Example 2 except for the use of each alcohol solvent as shown in Table 1 in place of n-butanol, crystalline L-tert-leucine was collected from 400 g of an aqueous solution containing L-tert-leucine and D-tert-leucine amide obtained in Reference Example 1. Table 1 shows the water content, crystallization temperature, and yield of L-tert-leucine of each alcohol solution after solvent substitution.

TABLE 1

| Alcohol solvent | Water content (% by mass) | Crystallization temperature (° C.) | Yield of L-tert-leucine (%) |
|---|---|---|---|
| Isobutyl alcohol | 0.4 | 20 | 95 |
| 1-Pentanol | 0.1 | 30 | 95 |
| Cyclohexanol | 0.2 | 25 | 88 |

EXAMPLE 8 n-butanol, 100 g, was added to 200 g (in total) of solution (water content of 24%) of 70 g of D-tert-leucine amide (optical purity>99% ee) and 2 g of L-tert-leucine (optical purity>99% ee) dissolved in 48 g of water and 80 g of isopropyl alcohol. The resultant mixture was concentrated to 150 g (in total) at 60° C. and 80 torr.

Potassium hydroxide (equivalent in quantity to amino acid and 20% by mole to amide), 4.9 g, and 145 g of n-butanol were added thereto, and the mixture was stirred at room temperature for 1 hour, thereby dissolving potassium hydroxide (300 g in total). The water content was 6%.

Further, the solution was concentrated to 150 g (in total) at 80° C. and 80 torr. Thereafter, 150 g of n-butanol was added thereto to bring the total amount to 300 g (water content of 0.1%). The solution was stirred at 120° C. for 6 hours.

As a result, while the amino acid ratio before the reaction was 2.8% (w/w), it was 5.4% (w/w) after the reaction.

After the reaction, the solution was concentrated to 100 g (in total), 100 g of n-heptane was added, and precipitated crystals were subjected to centrifugal filtration, followed by drying. Thus, 63 g of racemic tert-leucine amide was obtained. The concentrations of tert-leucine and tert-leucine amide were analyzed in accordance with analytical condition 3 of high performance liquid chromatography (HPLC) and the optical densities were independently analyzed according to analytical condition 4 of HPLC.

Analytical condition 3 of HPLC:
  Column: Inertsil ODS-3V (4.6φ×250 mm)
  Mobile phase: 0.1% aqueous solution of phosphoric acid
  Flow rate: 1 mL/min
  Detection: RI
Analytical condition 4 of HPLC:
  Column: SUMICHIRAL OA-5000 (4.6φ×250 mm)
  Mobile phase: water-methanol (85:15)
  Flow rate: 1 mL/min
  Detection: UV 254 nm As a result of HPLC analysis under the above conditions, the amount of tert-leucine contained in the collected tert-leucine amide was 0.13% (w/w). The yield of amino acid amide was 90% and the rate of racemization was 99%.

EXAMPLE 9 n-butanol, 100 g, was added to 200 g (in total) of a solution (water content of 22%) of 70 g of D-tert-leucine amide (optical purity>99% ee) and 5.5 g of L-tert-leucine (optical purity>99% ee) dissolved in 44 g of water and 80 g of isopropyl alcohol. The resultant mixture was concentrated to 150 g (in total) at 60° C. and 80 torr.

Potassium hydroxide (equivalent in quantity to amino acid and 20% by mole to amide), 9.87 g, and 140 g of n-butanol were added thereto, and the mixture was stirred at room temperature for 1 hour, thereby dissolving potassium hydroxide (300 g in total). The water content was 4%.

Further, the solution was concentrated to 150 g (in total) at 80° C. and 80 torr. Thereafter, 150 g of n-butanol was added thereto to bring the total amount to 300 g (water content of 0.1%). The solution was stirred at 120° C. for 6 hours.

As a result, while the amino acid ratio before the reaction was 7.3% (w/w), it was 11.9% (w/w) after the reaction.

After the reaction, the solution was concentrated to 100 g (in total), 100 g of n-heptane was added, and precipitated crystals were subjected to centrifugal filtration, followed by drying. Thus, 63 g of racemic tert-leucine amide was obtained.

As a result of HPLC analysis under the conditions given in Example 8, the amount of tert-leucine contained in the collected tert-leucine amide was 1.07% (w/w). The yield of amino acid amide was 89% and the rate of racemization was 99%.

EXAMPLE 10 n-butanol, 100 g, was added to 200 g (in total) of a solution (water content of 22%) of 70 g of D-tert-leucine amide (optical purity>99% ee) and 5.5 g of L-tert-leucine (optical purity>99% ee) dissolved in 44 g of water and 80 g of isopropyl alcohol. The resultant mixture was concentrated to 150 g (in total) at 60° C. and 80 torr. Thereafter, 150 g of n-butanol was added thereto to bring the total amount to 300 g. The water content was 4%.

Further, the solution was concentrated to 150 g (in total) at 80° C. and 80 torr. Thereafter, 150 g of n-butanol was added thereto to bring the total amount to 300 g. The water content was 0.1%.

tert-butoxypotassium (equivalent in quantity to amino acid and 10% by mole to amide), 10.74 g, was added thereto, and the mixture was stirred at 120° C. for 6 hours.

As a result, while the amino acid ratio before the reaction was 7.3% (w/w), it was 9.4% (w/w) after the reaction.

After the reaction, the solution was concentrated to 100 g (in total), 100 g of n-heptane was added, and precipitated crystals were subjected to centrifugal filtration, followed by drying. Thus, 63 g of racemic tert-leucine amide was obtained.

As a result of HPLC analysis under the conditions given in Example 8, the amount of tert-leucine contained in the collected tert-leucine amide was 0.89% (w/w). The yield of amino acid amide was 89% and the rate of racemization was 96%.

COMPARATIVE EXAMPLE 1 n-butanol, 100 g, was added to 200 g of a solution (water content of 22%) of 70 g of D-tert-leucine amide (optical purity>99% ee) and 5.5 g of L-tert-leucine (optical purity>99% ee) dissolved in 44 g of water and 80 g of isopropyl alcohol. The resultant mixture was concentrated to 150 g (in total) at 60° C. and 80 torr.

Sodium hydroxide (equivalent in quantity to amino acid and 20% by mole to amide), 6.00 g, and 144 g of n-butanol were added thereto, and the mixture was stirred at room temperature for 1 hour, thereby dissolving sodium hydroxide (total amount of 300 g). The water content was 4%.

Further, the solution was concentrated to 150 g (in total) at 80° C. and 80 torr. Thereafter, 150 g of n-butanol was added thereto to bring the total amount to 300 g (water content of 0.1%). The solution was stirred at 120° C. for 6 hours.

As a result, while the amino acid ratio before the reaction was 7.3% (w/w), it was 12.1% (w/w) after the reaction.

After the reaction, the solution was concentrated to 100 g (in total), 100 g of n-heptane was added, and precipitated crystals were subjected to centrifugal filtration, followed by drying. Thus, 65 g of racemic tert-leucine amide was collected.

As a result of HPLC analysis under the conditions given in Example 8, the amount of tert-leucine contained in the collected tert-leucine amide was 5.96% (w/w). The yield of amino acid amide was 87% and the rate of racemization was 98%.

REFERENCE EXAMPLE 2

Preparation of an Aqueous Solution Containing Optically Active α-amino Acid and Optically Active α-amino Acid Amide In accordance with the process described in JP Patent Application Laying Open (Kokai) No. 62-55097, *Enterobacter cloacae* N-7901 (FERM BP-873) was cultured. This culture solution, 500 mL, was centrifuged, and the wet cells were then suspended in distilled water to prepare a 1,140 g cell suspension. D, L-phenylalanine amide, 60 g, was dissolved in this suspension, and the mixture was then allowed to react at 40° C. for 24 hours. After the reaction, cells were removed by centrifugation and 1,150 g of an aqueous solution containing 2.5% by mass each of L-phenylalanine and D-phenylalanine amide was obtained.

The concentrations of phenylalanine and phenylalanine amide were analyzed according to analytical condition 5 of HPLC and each of the optical purity was independently analyzed according to analytical condition 6 of HPLC.
Analytical condition 5 of HPLC:
  Column: Inertsil ODS-3V (4.6φ×250 mm)
  Mobile phase: 0.1% aqueous solution of phosphoric acid-methanol (80:20)
  Flow rate: 1 mL/min
  Detection: UV 254 nm
Analytical condition 6 of HPLC:
  Column: SUMICHIRAL OA-5000 (4.6φ×250 mm)
  Mobile phase: water-methanol (70:30)
  Flow rate: 1 mL/min
  Detection: UV 254 nm

EXAMPLE 11

An aqueous solution containing L-phenylalanine and D-phenylalanine amide, 1100 g, obtained in Reference Example 2 was vacuum concentrated to 310 g. Thereafter, 770 g of n-butanol was added to the solution. The solution was further vacuum concentrated to obtain a final concentrate of 335 g. The water content of the concentrate was 0.2% by mass. After this concentrate was stirred at 70° C. for 1 hour, it was cooled and stirred at 40° C. for an additional 1 hour. Precipitated crystals were collected by centrifugal filtration and 28.2 g (dry mass) of L-phenylalanine was obtained (yield 94%). The amount of D-phenylalanine amide contained in the crystalline L-phenylalanine was 0.07% by mass.

EXAMPLE 12

After the centrifugal filtration in Example 11, 300 g of an n-butanol solution containing 28 g of D-phenylalanine amide was obtained. Potassium hydroxide, 1.1 g, and 50 g of n-butanol were added thereto, and the solution was then vacuum concentrated to 187 g. The water content of the concentrate was 0.05% by mass. After the concentrate was heated under reflux for 1 hour, the reaction solution was vacuum concentrated to 55 g, 100 g of toluene was added to the concentrate, and the mixture was stirred at 5° C. for 3 hours. Precipitated crystals were collected by suction filtration and 23.8 g (dry mass) of the mixture of D- and L-phenylalanine amide was obtained (yield from the separated mother liquor: 85%). The abundance ratio of crystalline D-phenylalanine amide to crystalline L-phenylalanine amide was 50.1:49.9.

EXAMPLE 13

Crystal of the mixture of D- and L-phenylalanine amide, 20 g, obtained in Example 12 was mixed with 380 g of the cell suspension prepared in Reference Example 2, and cell reaction was carried out in the same manner as in Reference Example 2. Twenty four hours later, the reaction solution contained 2.5% by mass each of L-phenylalanine and D-phenylalanine amide.

REFERENCE EXAMPLE 3

Preparation of an Aqueous Solution Containing Optically Active α-amino Acid and Optically Active α-amino Acid Amide In accordance with the process described in JP Patent Application Laying Open (Kokai) No. 62-55097, *Enterobacter cloacae* N-7901 (FERM BP-873) was cultured. This culture solution, 100 mL, was centrifuged, and the wet cells were then suspended in distilled water to prepare a 270 g cell suspension. D, L-phenylglycine amide, 30 g, was dissolved in this suspension, and the mixture was then allowed to react at 40° C. for 18 hours. After the reaction, cells were removed by centrifugation and 295 g of an aqueous solution containing 5.0% by mass each of L-phenylglycine and D-phenylglycine amide was obtained.

The concentrations of L-phenylglycine and D-phenylglycine amide were analyzed according to analytical condition 7 of HPLC and the optical purity was independently analyzed according to analytical condition 8 of HPLC.
Analytical condition 7 of HPLC:
  Column: Inertsil ODS-3V (4.6φ×250 mm)
  Mobile phase: 0.1% aqueous solution of phosphoric acid-methanol (95:5)
  Flow rate: 1 mL/min
  Detection: UV 220 nm
Analytical condition 8 of HPLC:
  Column: SUMICHIRAL OA-5000 (4.6φ×250 mm)
  Mobile phase: water-methanol (85:15)
  Flow rate: 1 mL/min
  Detection: UV 254 nm

EXAMPLE 14

An aqueous solution containing L-phenylglycine and D-phenylglycine amide, 295 g, obtained in Reference Example 3 was vacuum concentrated to 100 g. Thereafter, 190 g of n-butanol was added to the solution. The solution was vacuum concentrated to 110 g, 190 g of n-butanol was added again, and vacuum concentration was continued until 120 g of concentrate was finally obtained. After 30 g of n-butanol was added to the concentrate, the water content of the solution was 0.1% by mass. After this n-butanol solution was stirred at 70° C. for 1 hour, the solution was cooled and stirred at 20° C. for an additional 5 hours. Precipitated crystals were collected by suction filtration and 13.5 g (dry mass) of L-phenylglycine was obtained (yield 90%). The amount of D-phenylglycine amide contained in crystalline L-phenylglycine was 0.05% by mass.

EXAMPLE 15

After the centrifugal filtration in Example 14, 110 g of an n-butanol solution containing 14.5 g of D-phenylglycine amide was obtained. Potassium hydroxide, 0.2 g, and 40 g of n-butanol were added thereto, and the solution was then vacuum concentrated to 72 g. The water content of the concentrate was 0.08% by mass. After the concentrate was heated under reflux for 2 hours, the reaction solution was vacuum concentrated to 25 g, 40 g of toluene was added to the concentrate, and the mixture was stirred at 5° C. for 10 hours. Precipitated crystals were collected by suction filtration and 10.9 g (dry mass) of the mixture of D- and L-phenylglycine amide was obtained (yield from the separated mother liquor: 75%). The abundance ratio of crystalline D-phenylglycine amide to crystalline L-phenylglycine amide was 50.0:50.0.

EXAMPLE 16

The crystal of the mixture of D- and L-phenylglycine amide, 4 g, obtained in Example 15 was mixed with 36 g of the cell suspension prepared in Reference Example 3, and cell reaction was carried out in the same manner as in Reference Example 3. 24 hours later, the reaction solution contained 2.5% by mass each of L-phenylglycine and D-phenylglycine amide.

REFERENCE EXAMPLE 4

Preparation of an Aqueous Solution Containing Optically Active α-amino Acid and Optically Active α-amino Acid Amide In accordance with the process described in JP Patent Application Laying Open (Kokai) No. 62-55097, *Enterobacter cloacae* N-7901 (FERM BP-873) was cultured. This culture solution, 100 mL, was centrifuged, and the wet cells were then suspended in distilled water to prepare a 228 g cell suspension. D, L-p-fluoro-phenylglycine amide was dissolved in this suspension, and the mixture was then allowed to react at 40° C. for 24 hours. After the reaction, cells were removed by centrifugation and 230 g of an aqueous solution containing 2.5% by mass each of L-p-fluoro-phenylglycine and D-p-fluoro-phenylglycine amide was obtained.

The concentrations of L-p-fluoro-phenylglycine and D-p-fluoro-phenylglycine amide were analyzed according to analytical condition 9 of HPLC and each of the optical purity was independently analyzed according to analytical condition 10 of HPLC.
Analytical condition 9 of HPLC:
  Column: Inertsil ODS-3V (4.6φ×250 mm)
  Mobile phase: 0.1% aqueous solution of phosphoric acid-methanol (95:5)
  Flow rate: 1 mL/min
  Detection: UV 220 nm
Analytical condition 10 of HPLC:
  Column: SUMICHIRAL OA-5000 (4.6φ×250 mm)
  Mobile phase: water-methanol (85:20)
  Flow rate: 1 mL/min
  Detection: UV 254 nm

EXAMPLE 17

The aqueous solution containing L-p-fluoro-phenylglycine and D-p-fluoro-phenylglycine amide, 230 g, obtained in Reference Example 4 was vacuum concentrated to 60 g. Thereafter, 170 g of n-butanol was added to the solution. The solution was further vacuum concentrated to obtain a final concentrate of 60 g. After 60 g of n-butanol was added to the concentrate, the water content of the solution was 0.08% by mass. After this n-butanol solution was stirred at 70° C. for 1 hour, the solution was cooled and stirred at 20° C. for an additional 5 hours. Precipitated crystals were collected by centrifugal filtration and 5.4 g (dry mass) of L-p-fluoro-phenylglycine was obtained (yield 90%). The amount of D-p-fluoro-phenylglycine amide contained in the crystalline L-p-fluoro-phenylglycine was 0.1% by mass.

EXAMPLE 18

After the centrifugal filtration in Example 17, 110 g of an n-butanol solution containing 5.9 g of D-p-fluoro-phenylglycine amide was obtained. Potassium hydroxide, 0.2 g, was added thereto, and the solution was then vacuum concentrated to 60 g. The water content of the concentrate was 0.02% by mass. After the concentrate was heated under reflux for 2 hours, the reaction solution was vacuum concentrated to 20 g, 20 g of toluene was added to the concentrate, and the mixture was stirred at 5° C. for 3 hours. Precipitated crystals were collected by suction filtration and 4.4 g (dry mass) of the mixture of D- and L-p-fluoro-phenylglycine amide was obtained (yield from the separated mother liquor: 74%). The abundance ratio of the crystalline D-p-fluoro-phenylglycine amide to crystalline L-p-fluoro-phenylglycine amide was 50.0:50.0.

EXAMPLE 19

Crystal of the mixture of D- and L-p-fluoro-phenylglycine amide, 4 g, obtained in Example 18 was mixed with 36 g of the cell suspension prepared in Reference Example 4, and cell reaction was carried out in the same manner as in Reference Example 4. The reaction solution contained 2.5% by mass each of L-p-fluoro-phenylglycine and D-p-fluoro-phenylglycine amide 24 hours later.

REFERENCE EXAMPLE 5

Preparation of an Aqueous Solution Containing Optically Active α-amino Acid and Optically Active α-amino Acid Amide In the same manner as in Reference Example 4, 12 g of D, L-o-chloro-phenylglycine amide was dissolved in 228 g of *Enterobacter cloacae* N-7901 (FERM BP-873) suspension. Thereafter, the solution was allowed to react at 40° C. for 24 hours. After the reaction, cells were removed by centrifugation and 230 g of an aqueous solution containing 2.5% by mass each of L-o-chloro-phenylglycine and D-o-chloro-phenylglycine amide was obtained.

EXAMPLE 20

The aqueous solution containing L-o-chloro-phenylglycine and D-o-chloro-phenylglycine amide, 230 g, obtained in Reference Example 5 was processed in the same manner as in Example 17, and 5.5 g (dry mass) of L-o-chloro-phenylglycine was obtained (yield 91%). The amount of D-o-chloro-phenylglycine amide contained in crystalline L-o-chloro-phenylglycine was 0.1% by mass.

EXAMPLE 21

After the procedure in Example 20, 110 g of an n-butanol solution containing 5.9 g of D-o-chloro-phenylglycine amide was obtained. Potassium hydroxide, 0.2 g, was added thereto, followed by the same procedures as in Example 18, 4.5 g (dry mass) of DL-o-chloro-phenylglycine amide enantiomer was obtained (yield from separated mother liquor: 76%). The abundance ratio of crystalline D-o-chloro-phenylglycine amide to crystalline L-o-chloro-phenylglycine amide was 50.0:50.0. Using the crystals, cell reaction was carried out in the same manner as in Example 19. As a result, 24 hours later, the reaction solution contained 2.5% by mass each of L-o-chloro-phenylglycine and D-o-chloro-phenylglycine amide.

REFERENCE EXAMPLE 6

Preparation of an Aqueous Solution Containing Optically Active α-amino Acid and Optically Active α-amino Acid Amide In the same manner as in Reference Example 4, 12 g of DL-p-hydroxy-phenylalanine amide was dissolved in 228 g of *Enterobacter cloacae* N-7901 (FERM BP-873) suspension. Thereafter, the solution was allowed to react at 40° C. for 24 hours. After the reaction, cells were removed by centrifugation and 230 g of an aqueous solution containing 2.5% by mass each of L-p-hydroxy-phenylalanine and D-p-hydroxy-phenylalanine amide was obtained.

EXAMPLE 22

The aqueous solution containing L-p-hydroxy-phenylalanine and D-p-hydroxy-phenylalanine amide, 230 g, obtained in Reference Example 6 was subjected to the same procedure as in Example 17, and 5.3 g (dry mass) of L-p-hydroxy-phenylalanine was obtained (yield 88%). The amount of D-p-hydroxy-phenylalanine amide contained in the crystalline L-p-hydroxy-phenylalanine was 0.2% by mass.

EXAMPLE 23

After the procedure in Example 22, 110 g of an n-butanol solution containing 5.9 g of D-p-hydroxy-phenylalanine amide was obtained. Potassium hydroxide, 0.3 g, was added thereto, followed by the same procedures as in Example 18, and 4.2 g (dry mass) of the mixture of D- and L-p-hydroxy-phenylalanine amide was obtained (yield from separated mother liquor: 72%). The abundance ratio of D-p-hydroxy-phenylalanine amide to L-p-hydroxy-phenylalanine amide was 50.0:50.0. Using the resuntantcrystals, cell reaction was carried out in the same manner as in Example 19. As a result, 24 hours later, the reaction solution contained 2.5% by mass each of L-p-hydroxy-phenylalanine and D-p-hydroxy-phenylalanine amide.

REFERENCE EXAMPLE 7

Preparation of an Aqueous Solution Containing Optically Active α-amino Acid and Optically Active α-amino Acid Amide In accordance with the process described in JP Patent Application Laying Open (Kokai) No. 62-55097, *Enterobacter cloacae* N-7901 (FERM BP-873) was cultured. This culture solution, 100 mL, was centrifuged, and the wet cells were then suspended in distilled water to prepare a 240 g cell suspension. After 10 g of DL-2-amino-n-lactic acid amide was dissolved in this suspension, the solution was allowed to react at 40° C. for 40 hours. After the reaction, cells were removed by centrifugation, and 240 g of an aqueous solution containing 2.0% by mass each of L-2-amino-n-lactic acid and D-2-amino-n-lactic acid amide was obtained.

EXAMPLE 24

The aqueous solution containing L-2-amino-n-lactic acid and D-2-amino-n-lactic acid amide, 240 g, obtained in Reference Example 7 was vacuum concentrated to 50 g. Thereafter, 180 g of n-butanol was added to the solution. The solution was further vacuum concentrated to obtain a final concentrate of 50 g. After 50 g of n-butanol was added to the concentrate, the water content of the solution was 0.07% by mass. After the n-butanol solution was stirred at 70° C. for 1 hour, the solution was cooled and stirred at 30° C. for an additional 3 hours. Precipitated crystals were collected by suction filtration and 4.0 g (dry mass) of L-2-amino-n-lactic acid was obtained (yield 90%). The amount of D-2-amino-n-lactic acid amide contained in crystalline L-2-amino-n-lactic acid was 0.2% by mass.

EXAMPLE 25

After the procedure in Example 24, 85 g of an n-butanol solution containing 4.8 g of D-2-amino-n-lactic acid amide was obtained. Potassium hydroxide, 0.1 g, was added thereto, and the solution was then vacuum concentrated to 25 g. The water content of the concentrate was 0.09% by mass. After the concentrate was heated under reflux for 7 hours, the reaction solution was vacuum concentrated to 8 g, 8 g of toluene was further added to the concentrate, and the mixture was stirred at 0° C. for 3 hours. Precipitated crystals were collected by suction filtration, and 3.4 g (dry mass) of the mixture of D- and L-2-amino-n-lactic acid amide was obtained (yield from the separated mother liquor: 70%). The abundance ratio of crystalline D-2-amino-n-lactic acid amide to crystalline L-2-amino-n-lactic acid amide was 50.0:50.0.

EXAMPLE 26

The crystal of the mixture of D- and L-2-amino-n-lactic acid amide, 2 g, obtained in Example 25 was mixed with 48 g of the cell suspension prepared in Reference Example 2, and cell reaction was carried out in the same manner as in Reference Example 7. 24 hours later, the reaction solution contained 2.0% by mass each of L-2-amino-n-lactic acid and D-2-amino-n-lactic acid amide.

REFERENCE EXAMPLE 8

Preparation of an Aqueous Solution Containing Optically Active α-amino Acid and Optically Active α-amino Acid Amide In the same manner as in Reference Example 7, 10 g of D-isoleucine amide was dissolved in 240 g of *Enterobacter cloacae* N-7901 (FERM BP-873) suspension. The solution was then allowed to react at 40° C. for 40 hours. After the reaction, cells were removed by centrifugation and 240 g of an aqueous solution containing 2.0% by mass each of L-isoleucine and D-isoleucine amide was obtained.

EXAMPLE 27

The aqueous solution containing L-isoleucine and D-isoleucine amide, 240 g, obtained in Reference Example 8, was processed in the same manner as in Example 24, and 4.5 g (dry mass) of L-isoleucine was obtained (yield 88%). The amount of D-isoleucine amide contained in crystalline L-isoleucine was 0.2% by mass.

EXAMPLE 28

After the procedure in Example 27, 85 g of an n-butanol solution containing 4.8 g of D-isoleucine amide was obtained. Potassium hydroxide, 0.2 g, was added thereto, followed by the same procedures as in Example 18, and 3.6 g (dry mass) of the mixture of D- and L-isoleucine amide was obtained (yield from separated mother liquor: 75%).

The abundance ratio of crystalline D-isoleucine amide to crystalline L-isoleucine amide was 51.0:49.0. Using these crystals, cell reaction was carried out in the same manner as in Example 26. As a result, 40 hours later, the reaction solution contained 2.0% by mass each of L-isoleucine and D-isoleucine amide.

COMPARATIVE EXAMPLE 2

The same procedure as in Example 3 was carried out except that ethanol was used instead of n-butanol. An aqueous solution containing L-tert-leucine and D-tert-leucine amide, 500 g obtained in Reference Example 1, was vacuum concentrated to 250 g, and 250 g of ethanol was then added to the solution. The solution was further vacuum concentrated, and 250 g of ethanol was added again to the solution when the amount of the distillate became 240 g. After the addition, vacuum concentration was carried out again to obtain a final concentrate of 350 g. The water content of the concentrate was 19.5% by mass. 250 g of ethanol was further added and vacuum concentration was carried out again. When the amount of the distillate became 240 g, 250 g of ethanol was added again. This series of operations was carried out again, and 340 g of concentrate (water content of 4.0% by mass) was obtained. The total amount of ethanol used was 3,000 g. In the same manner as in Example 3, crystals were precipitated and subjected to centrifugal filtration. Thereafter, 59.6 g (dry mass) of white crystals were obtained. The abundance ratio of L-tert-leucine to D-tert-leucine amide in the crystal was 68.5:31.5.

COMPARATIVE EXAMPLE 3

Potassium hydroxide, 1.3 g, was added to 150 g of an ethanol solution containing 20 g of D-tert-leucine amide, and the resultant solution was heated under reflux for 6 hours. Racemization, however, did not substantially proceed, and the amount of L-tert-leucine amide in the collected crystals after concentration and crystallization was insignificant while D-tert-leucine amide accounted for 99% or more.

INDUSTRAIL APPLICABILITY

Optically active α-amino acid can be produced with very high yield as follows: in an aqueous medium, racemic α-amino acid amide is contacted with cells or enzymes having an ability to stereospecifically hydrolyse α-amino acid amide; a water solvent is substituted with at least one solvent selected from linear, branched, or cyclic alcohol having 3 or more carbon atoms; and the optically active α-amino acid is preferentially precipitated from the resultant alcohol solution.

When amino acid amide is purified from the alcohol solution containing optically active α-amino acid amide which is obtained after separating the optically active α-amino acid, the use of basic compounds, particularly potassium compounds, results in the improved amino acid solubility in an organic solvent and separation of amino acid amide with high purity, thereby easily preparing the separated amino acid amide for racemization. Thus, the production efficiency of optically active α-amino acid can be improved.

All publications cited herein are incorporated herein in its entirety. It is obvious to those skilled in the art that various modifications and variations of the present invention are feasible within the technical scope of the invention described in the accompanying claims. The present invention includes such modifications and variations.

What is claimed is:

1. A process for producing an optically active α-amino acid and optically active α-amino acid amide which comprises:
    substituting a water solvent of an aqueous solution containing an optically active α-amino acid and a corresponding optically active α-amino amide with n-butanol, and
    wherein the α-amino acid is represented by formula (I):

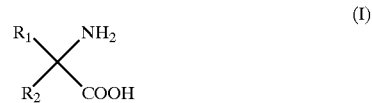

(I)

wherein $R_1$ and $R_2$ maybe the same or different and are selected from the group consisting of a hydrogen atom, lower alkyl, substituted lower alkyl, lower alkenyl, substituted lower alkenyl, cycloalkyl, phenyl, substituted phenyl, heterocycle, and substituted heterocycle; and the α-amino amide is represented by formula (II):

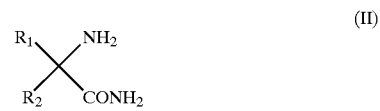

(II)

wherein $R_1$ and $R_2$ may be the same or different and are selected from the group consisting of a hydrogen atom, lower alkyl, substituted lower alkyl, lower alkenyl, substituted lower alkenyl, cycloalkyl, phenyl, substituted phenyl, heterocyole, and substituted heterocycle, wherein the $R_1$ and $R_2$ substituents in formula (I) and formula (II) are the same.

2. The process of claim 1, wherein the α-amino acid and the corresponding α-amino acid amide are respectively represented by formula (III) and (IV) below:

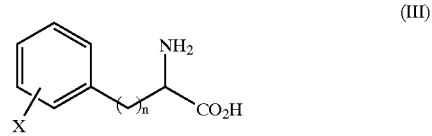

(III)

wherein n is 0 to 1 and X represents hydrogen, halogen, alkyl, hydroxyl, and alkoxy;

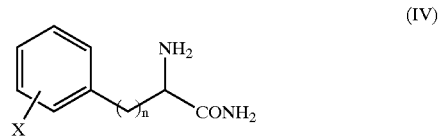

(IV)

wherein n is 0 to 1 and X represents hydrogen, halogen, alkyl, hydroxyl, and alkoxy; and wherein the n and X in formulas (III) and (IV) are the same.

3. The process of claim 1, wherein the α-amino acid and the α-amino acid amide are selected from the group consisting of α-tert-leucine and α-tert-leucine amide; α-phenylalanine and α-phenylalanine amide; α-phenylglycine and α-phenylglycine amide; α-p-fluorophenylglycine and α-p-fluoro-phenylglycine amide; α-o-chloro-phenylglycine and α-o-chloro-phenylglycine amide; α-p-hydroxy-phenylalanine and α-p-hydroxy-phenylalanine amide; α-2-amino-n-lactic acid and α-2-amino-n-lactic acid amide; and α-isoleucine and α-isoleucine amide.

4. The process of claim 1, wherein the aqueous solution containing the optically active α-amino acid and the optically active α-amino acid amide is obtained by contacting at least one optically impure α-amino acid amide with cells or processed cells thereof having an ability to asymmetrically hydrolyse.

5. The process of claim 1 wherein the water content of the separated mother liquor after the precipitation of the optically active α-amino acid is 10% by mass or lower.

6. The process of claim 4, wherein the water content of the separated mother liquor after the precipitation of the optically active α-amino acid is 10% by mass or lower.

7. The process of claim 1, further comprising:
(i) precipitating the optically active α-amino acid from the alcohol solution precipitate of optically active α-amino acids and a mother liquor,
(ii) removing the precipitate and adding potassium hydroxide or tert-butoxypotassium to the separated mother liquor, racemizing, and then precipitating the α-amino acid amide preferentially from the solution, and
(iii) producing the optically active α-amino acid and the optically active α-amino acid amide by contacting the α-amino acid amide obtained by the step (ii) with cells or processed cells thereof having an ability to asymmetrically hydrolyse said α-amino acid amide.

8. The process of claim 7, wherein said aqueous solution containing the optically active α-amino acid and optically active α-amino acid amide has been obtained by contacting an optically impure α-amino acid amide with cells which have an ability to asymmetrically hydrolyze said optically impure α-amino acid amide.

9. The process of claim 7, wherein said aqueous solution containing the optically active α-amino acid and optically active α-amino acid amide has been obtained by contacting an optically impure α-amino acid amide with processed cells selected from the group consisting of homogenized cells, cell extract, crude or purified enzyme and immobilized cell products, which have an ability to asymmetrically hydrolyze said optically impure α-amino acid amide.

10. The process of claim 7, wherein the water content of the separated mother liquor after the precipitation of the optically active α-amino acid is 10% by mass or lower.

11. The process of claim 7, wherein the amino acid content in the precipitated crystalline amino acid amide is 1.5% or lower.

12. The process of claim 8, wherein the amino acid content in the precipitated crystalline amino acid amide is 1.5% or lower.

13. The process of claim 9, wherein the amino acid content in the precipitated crystalline amino acid amide is 1.5% or lower.

14. The process of claim 10, wherein the amino acid content in the precipitated crystalline amino acid amide is 1.5% or lower.

15. The process of claim 1, wherein the α-amino and corresponding α-amino acid amide are respectively represented by formulas (V) and (VI) below:

wherein R represents linear or branched alkyl having 2 to 5 carbon atoms;

wherein R represents linear or branched alkyl having 2 to 5 carbon atoms, wherein R in formulas (V) and (VI) is the same.

16. The process of claim 1, wherein $R_1$ or $R_2$ is H.

17. The process of claim 1, wherein one of $R_1$ or $R_2$ is H, and the other is lower alkyl, lower alkenyl, cycloalkyl, or phenyl.

18. The process of claim 1, wherein one of $R_1$ or $R_2$ is H, and the other is a heterocycle or a substituted heterocycle.

19. The process of claim 1, wherein the amino acid and amino acid amide are leucine and leucine amide; isoleucine and isoleucine amide; or valine and valine amide.

20. The process of claim 1, wherein the amino acid and amino acid amide are methionine and methionine amide.

21. The process of claim 1, wherein the amino acid and amino acid amide are phenylalanine and phenylalanine amide.

22. The process of claim 1, wherein the amino acid and amino acid amide are tyrosine and tyrosine amide.

23. The process of claim 1, wherein the amino acid and amino acid amide are alanine and alanine amide; or serine and serine amide.

24. The process of claim 1, wherein the amino acid and amino acid amide are typtophan and tryptophan amide.

25. The process of claim 1, wherein the amino acid and amino acid amide are histidine and histidine amide; or lysine and lysine amide.

26. The process of claim 1, wherein the amino acid and amino acid amide are cysteine and cysteine amide.

27. A process for purifying an α-amino acid amide, which comprises:

substituting a water solvent of an aqueous solution containing at least one optically active α-amino acid and at least one optically active α-amino amide with n-butanol, precipitating the optically active α-amino acid from the alcohol solution, adding potassium hydroxide or tert-butoxypotassium to the separated mother liquor, in which optically active α-amino acids had been precipitated, recemizing, and then precipitating said α-amino acid amide preferentially from the solution;

wherein the α-amino acid is represented by formula (I):

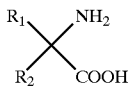

(I)

wherein $R_1$ and $R_2$ may be the same or different and are selected from the group consisting of a hydrogen atom, lower alkyl, substituted lower alkyl, lower alkenyl, substituted lower alkenyl, cycloalkyl, phenyl, substituted phenyl, heterocycle, and substituted heterocycle; and the α-amino amide is represented by formula (II):

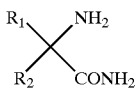

(II)

wherein $R_1$ and $R_2$ may be the same or different are selected from the group consisting of a hydrogen atom, lower alkyl, substituted lower alkyl, lower alkenyl, substituted lower alkenyl, cycloalkyl, phenyl, substituted phenyl, heterocycle, and substituted heterocycle; and wherein $R_1$ and $R_2$ in formulas (I) and (II) are the same.

28. The process of claim 27, wherein said aqueous solution containing the optically active α-amino acid and optically active α-amino acid amide has been obtained by contacting an optically impure α-amino acid amide with cells which have an ability to asymmetrically hydrolyze said optically impure α-amino acid amide.

29. The process of claim 27, wherein said aqueous solution containing the optically active α-amino acid and optically active α-amino acid amide has been obtained by contacting an optically impure α-amino acid amide with processed cells selected from the group consisting of homogenized cells, cell extract, crude or purified enzyme and immobilized cell products, which have an ability to asymmetrically hydrolyze said optically impure α-amino acid amide.

30. The process of claim 27, wherein the water content of the separated mother liquor after the precipitation of the optically active α-amino acid is 10% by mass or lower.

31. The process of claim 27, wherein the amino acid content in the precipitated crystalline amino acid amide is 1.5% or lower.

32. The process of claim 28, wherein the amino acid content in the precipitated crystalline amino acid amide is 1.5% or lower.

33. The process of claim 29, wherein the amino acid content in the precipitated crystalline amino acid amide is 1.5% or lower.

34. The process of claim 30, wherein the amino acid content in the precipitated crystalline amino acid amide is 1.5% or lower.

* * * * *